United States Patent [19]

Lessard

[11] Patent Number: 5,324,665
[45] Date of Patent: Jun. 28, 1994

[54] ON-LINE METHOD FOR MONITORING CHLORIDE LEVELS IN A FLUID STREAM

[75] Inventor: Ronald B. Lessard, Elmhurst, Ill.

[73] Assignee: Nalco Chemical Company, Naperville, Ill.

[21] Appl. No.: 978,118

[22] Filed: Nov. 18, 1992

[51] Int. Cl.⁵ .................. G01N 35/08; G01N 33/18; G01N 27/00
[52] U.S. Cl. .................. 436/55; 210/96.2; 210/739; 436/124; 436/125; 436/149; 436/150; 436/151; 436/175; 436/177; 204/153.13; 204/415
[58] Field of Search ........... 436/125, 124, 55, 149.151, 436/175, 177; 422/62; 210/96.2, 739; 204/153.13, 415

[56] References Cited

U.S. PATENT DOCUMENTS

| | | | |
|---|---|---|---|
| 4,814,281 | 3/1989 | Byers | 422/62 |
| 4,900,427 | 2/1990 | Weers et al. | 208/48 AA |
| 4,942,133 | 7/1990 | Pauly et al. | 436/125 |

FOREIGN PATENT DOCUMENTS

| | | |
|---|---|---|
| 2342496 | 9/1977 | France . |
| 3158458 | 7/1988 | Japan . |
| 1201850 | 8/1970 | United Kingdom . |

OTHER PUBLICATIONS

Laboratory Separation, Membrane Filtration, Chromatography Product Catalog, Amicon (a WR Grace Company) 1987, pp.52-53.

Primary Examiner—Jill A. Johnston
Assistant Examiner—Jan M. Ludlow
Attorney, Agent, or Firm—Hill, Steadman & Simpson

[57] ABSTRACT

A method for monitoring automatically, on-line chloride content in a fluid stream in an oil refinery. Additionally, the present invention provides a method for neutralizing the acids resulting from the chloride in a fluid stream. Pursuant to the method, a fluid sample is collected. To the sample is added a sulfide scavenger that will react with the sulfide that is present to create a reaction product. The fluid is then passed to a reaction or measurement cell including a chloride specific electrode. Prior to contacting the chloride specific electrode, the fluid must pass through a membrane that prevents the reaction product from flowing therethrough. The fluid that flows through the membrane is allowed to contact the chloride specific electrode. This allows the chloride content to be monitored in the fluid. The concentration of chloride can then be used to generate a signal to control the addition of a neutralizing agent to the fluid stream.

17 Claims, 2 Drawing Sheets

ON-LINE METHOD FOR MONITORING CHLORIDE LEVELS IN A FLUID STREAM

BACKGROUND OF THE INVENTION

The present invention relates generally to methods for monitoring and neutralizing contaminants in a fluid stream. More specifically, the present invention relates to methods and apparatuses for monitoring and/or neutralizing chloride levels in fluid streams in oil refineries.

During the refinery process, crude oil introduced into distillation columns contains water, organic acids and chemical precursors to various strongly acidic species. Due to salts comprised of chloride that are cracked in the distillation process, chloride is present in such fluid streams.

Determining the concentration of the chloride, and neutralizing same, is critical because the chloride can form hydrochloric acid. Of course, hydrochloric acid is extremely corrosive and if not neutralized can damage piping and vessels that contain such fluids. Typically, hydrochloric acid is one of many acidic species that are generated in fluid streams at the distillation tower of petroleum refineries.

Various methods have been suggested to remedy acidic corrosion. Generally, a neutralizing agent is introduced, either directly to the crude charge and/or injected at the top of the distillation tower. The quantity of neutralizing agent to be added is usually determined following some manual sampling and acid analysis of the tower condensate or of some other species. Because the time elapse between these manual analyses may span one or more days, excursions in the acid concentrations of the overhead water may occur. Because of the rapidity of acid corrosion, even a one day's unmonitored and uncontrolled excursion can have serious consequences.

U.S. patent application Ser. No. 07/867,890, filed Apr. 13, 1992, entitled: "ON-LINE ACID MONITOR AND NEUTRALIZER FEED CONTROL OF THE OVERHEAD WATER IN OIL REFINERIES" discloses an apparatus and method for monitoring and controlling the concentration of acid in the overhead water of oil refineries. Although this system works very well at controlling acid concentration, it is desirable in at least some situations to have a system for also monitoring only chloride concentration and allowing the system disclosed in the above-identified patent application to measure and control other acid species.

It is presently very difficult to continuously measure the concentration of chloride in such fluid. For example, although chloride specific electrodes exist, these cannot typically be used efficiently in a fluid stream from a refinery. This is due to the fact that sulfide, which may also be present in the fluid stream, will interfere with the chloride specific electrode's measurement of chloride. This will result in the reporting of incorrect chloride concentrations.

Although attempts at resolving this problem have been tried, for example, U.S. Pat. No. 4,942,133, these attempts are not entirely satisfactory. For example, as disclosed in the U.S. Pat. No. 4,942,133, in order to analyze chloride ion content, the following procedure is utilized. Drawing from the overhead waters, a stream of water for analysis; removing from the sample so drawn, the hydrocarbons as well as the suspended matter; blowing nitrogen into the sample to sweep away the hydrogen sulfide and the residue hydrocarbons; oxidizing the $S^{2-}$ or $HS^-$ sulfide ions to sulfate ions; acidifying the sample; and finally measuring by a combined electrode, the content of chloride ions present. To the best of the inventor's knowledge, this system has not been commercialized, at least on a large scale.

There is therefore a need for a method for the automatic, on-line monitoring of chloride in fluid streams, especially in oil refineries, for the purpose of controlling corrosion.

SUMMARY OF THE INVENTION

The present invention provides a method for monitoring automatically, on-line chloride content in a fluid stream in an oil refinery. Additionally, the present invention provides a method for neutralizing chloride in a fluid stream.

Pursuant to the present invention, a fluid sample is collected. To the sample is added a sulfide scavenger that will react with the sulfide that is present, creating a reaction product. The fluid is then passed to a reaction, or measurement, cell that includes a chloride specific electrode. Prior to contacting the chloride specific electrode, the fluid must pass through a membrane that prevents the reaction product from flowing therethrough. The fluid that flows through the membrane is allowed to contact the chloride specific electrode. This allows the chloride content in the fluid to be monitored. Because the sulfides have been removed from the fluid that passes through the membrane they do not interfere with the measurement. The concentration of chloride can then be used to generate a signal to control the addition of a neutralizing agent to the fluid stream.

An advantage of the present invention is that it provides an automatic, on-line monitoring of chloride concentration in a fluid.

An additional advantage of the present invention is that the present invention can be utilized in a monitor/control system that can be used to automatically adjust a neutralizing feed pump.

Further, an advantage of the present invention is that it allows a neutralizing feed pump to be adjusted automatically in response to chloride content as opposed to typically used approximately once-a-day adjustments.

Moreover, the present invention provides an automatic system for measuring chloride concentration and adjusting the neutralizing feed and does not require an operator to do same.

Still further, an advantage of the present invention is that it provides an efficient system for neutralizing chloride in a fluid stream.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a method and apparatus for the automatic, on-line monitoring of chloride.

This allows one to determine chloride, and resulting hydrochloric acid, content in a fluid such as overhead water in oil refineries. This provides a system that can be used to automatically adjust the neutralizer that is fed into the fluid to neutralize the chloride.

Figure 1:
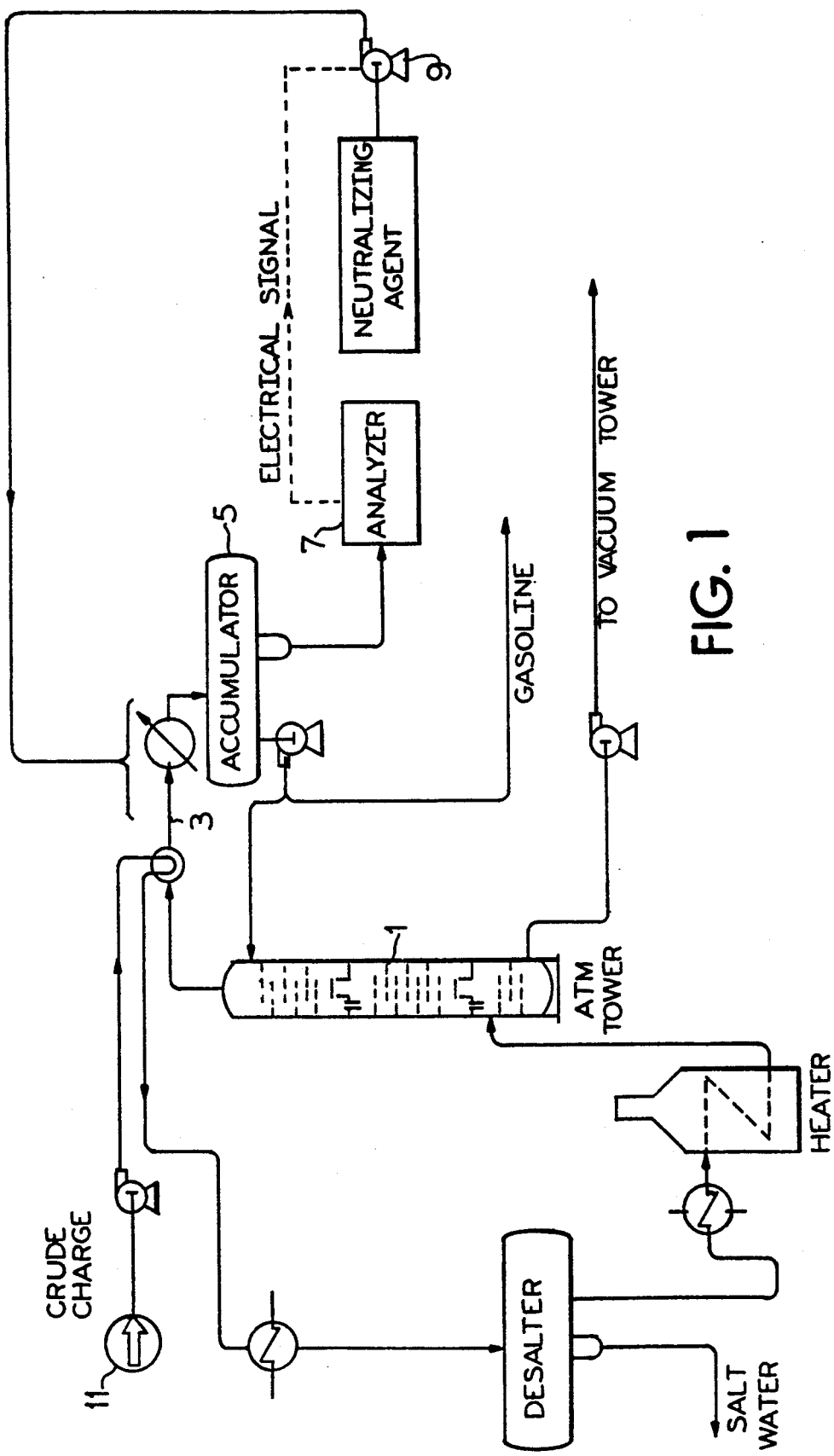
FIG. 1 illustrates a schematic flow diagram of a typical refinery distillation tower.

Referring to FIG. 1, following desalting, crude oil is processed in distillation column 1. The crude oil charge 11 introduced into these columns contains water, organic acids, and the chemical precursors to various strongly acidic species. During the distillation process, water vapor rises to the top of the distillation column. This water is referred to as "overhead water." At some point in the distillation tower/overhead vapor line, the water condenses. The temperature at which this condensation occurs is referred to as the "dew point."

Water condensed at the dew point is acidic with the primary source of this acid being hydrochloric acid generated from residual salt not removed during the desalting procedure. Generally, about 5% of the salt originally present will survive desalting. Hydrochloric acid may account for up to 95% of the total acid present.

Of course, these acids can cause corrosion problems. However, such acid corrosion problems can be reduced through the controlled addition of neutralizing agents. Pursuant to the present invention, the neutralizing agents may be introduced directly into the crude oil charge 11. Alternatively, they may be injected into a higher segment of the distillation tower, or into the overhead vapor line 3.

Generally, the present invention provides a system wherein a chloride specific electrode is utilized to determine chloride concentration in a fluid sample. If desired, a strong acid analyzer, such as that disclosed in U.S. patent application Ser. No. 07/867,890 can be used to determine the concentration of other acids in the overhead water.

Figure 2:
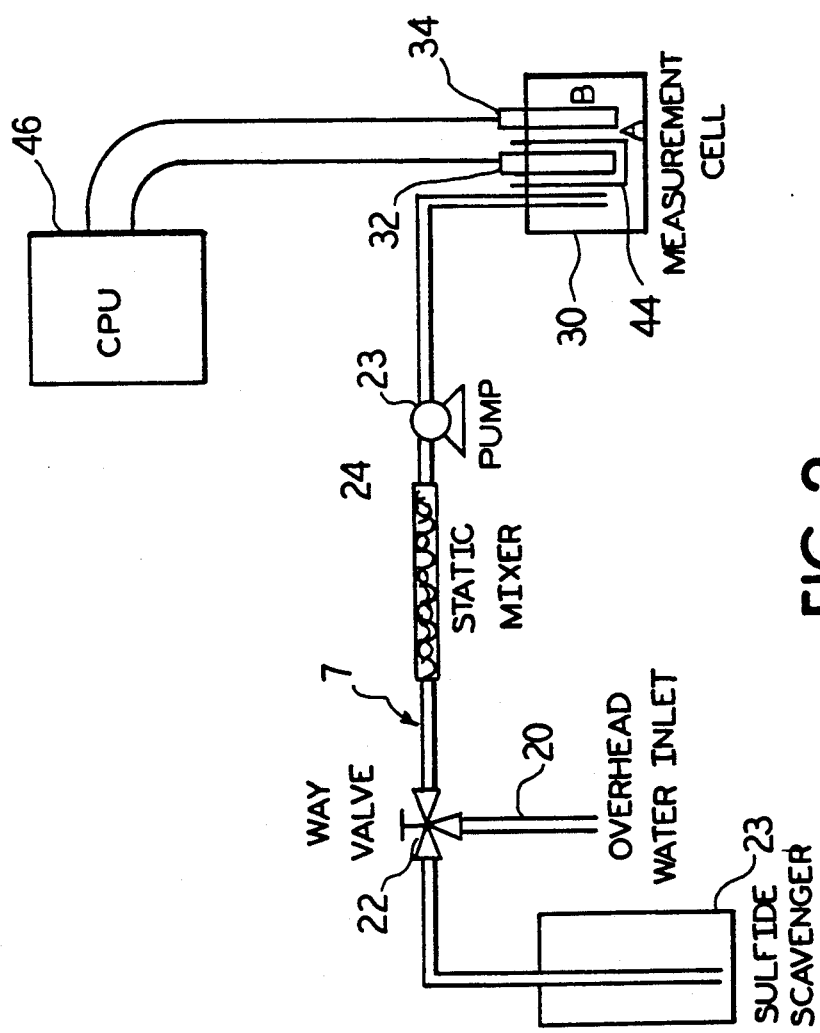
FIG. 2 illustrates a schematic of a system for determining chloride content.

Referring to FIG. 2, a schematic of the chloride monitoring system 7 is illustrated. Pursuant to the system, a predetermined amount of overhead water is removed through flow path 20. To control the flow of overhead water, a three-way valve 22 is used. To the sample of overhead water is added a sulfide scavenger 23. To insure that the sulfide scavenger reacts with any sulfide present, a mixer is provided in tubing 24. In the illustrated embodiment, a static mixer is used although any mixer can be used.

The sulfide scavenger used is one that functions by way of nucleophilic substitution. A number of sulfide scavengers are possible.

The sulfide scavenger can be a reaction product of morpholine and formaldehyde. Such sulfide scavengers are disclosed in U.S. patent application Ser. No. 07/805,755 filed Dec. 12, 1991, entitled: "PREVENTION OF CRACKING AND BLISTERING OF REFINERY STEELS BY CYANIDE SCAVENGING IN PETROLEUM REFINERY PROCESSES", the disclosure of which is hereby incorporated by reference. As set forth in that patent application, the reaction product of morpholine and formaldehyde is that reaction product that contains a 2 to 1 mole ratio of morpholine to formaldehyde. This reaction product has a structure illustrated in Formula I below:

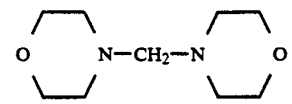

Formula I

The compound represented by Formula I may be referred to as bis-morpholinyl methane.

However, when manufacturing the chemical described as the 2 to 1 mole adduct in Formula 1, other reactions can occur, such that the materials represented as Formulas II and III below may also be formed:

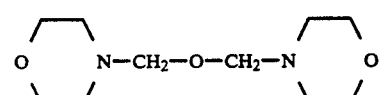

Formula II

Formula III

In a preferred embodiment, the sulfide scavenger has a molecular weight of approximately 500 or greater. For example, the following scavenger can be used.

It is important that all of the sulfide present in the overhead water is bound to the sulfide scavenger. Accordingly, preferably, an excess amount of sulfide scavenger is added to the overhead water sample. Most preferably, the sulfide scavenger is added in an amount that is 2 to 5 times the expected sulfide content.

Figure 3:
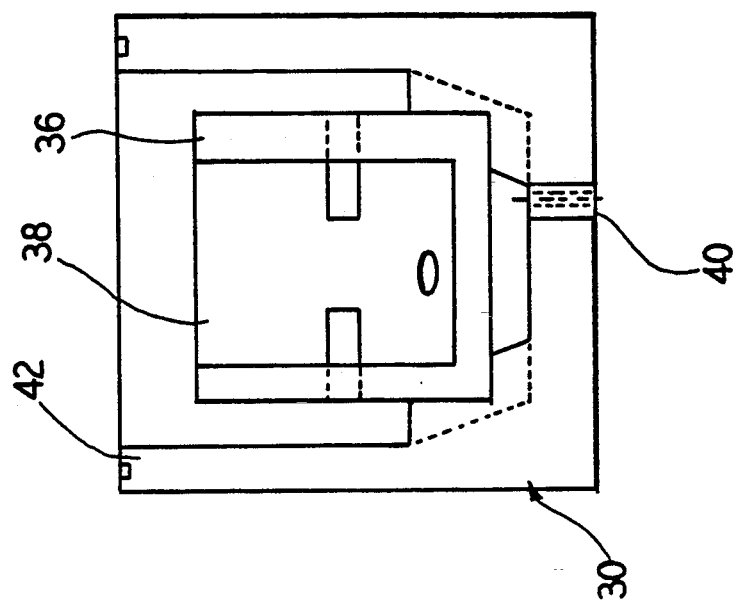
FIG. 3 illustrates a cross-sectional view of the measurement cell of the system of FIG. 2 with electrodes removed.

The overhead water including the sulfide scavenger is then fed via pump 28 to a measurement, or reaction, cell 30 including a chloride ion specific electrode 32 and a reference electrode 34. FIG. 3 illustrates a cross-sectional view of an embodiment of the measurement cell 30 with electrodes 32 and 34 removed. The measurement cell 30 includes a body 36 that houses the electrodes 32 and 34 and can receive fluid samples in a chamber 38 defined thereby. A drain 40 is provided at a bottom of the body 36 to allow the chamber 38 to be drained after a sample is tested. The body 36 is preferably housed in a drain cup 42.

As illustrated in FIG. 2, the overhead water is fed into the measurement cell 30. Pursuant to the present invention, the reaction product of the sulfide and sulfide scavenger is separated from the overhead sample and specifically the chloride ions by use of a membrane 44. In the embodiment illustrated, the membrane 44 surrounds the chloride ion specific electrode 32.

The inventors have found that a dialysis membrane such as a cellulose ester membrane can be used to prevent the reaction product, and thereby the sulfide, from contacting the chloride specific electrode 32. Such membranes are available from Spectra/Por of Houston, Tex. under the name Molecular Porous Membranes.

The molecular weight of the sulfide scavenger is an important consideration in constructing the system 7. In this regard, the membrane 44 is chosen to have a molecular weight cut-off that is less than the molecular weight of the reaction product of the sulfide scavenger and sulfide. The molecular weight cut-off defines what products will and will not diffuse through the membrane. It has been found with bis-morpholinyl methane that if a dialysis membrane is utilized with a molecular weight cut-off of 100 that chloride ions were freely passed through the membrane, but that the scavenged sulfides remained outside the membrane.

Of course, membranes having a greater molecular weight cut-off can be utilized. The larger the pore size of the membrane, i.e., the larger the molecular weight cut-off, the quicker the diffusion time. With a molecular weight cut-off of 100, the diffusion time may be up to approximately 12 hours. With a molecular weight cut-off of approximately 10,000, the diffusion time may be 15 minutes or less. Although it has not been tested, it is believed that at a molecular cut-off of 1,000, the diffusion time would be around 1 hour. The diffusion time is the time limiting factor with respect to the testing of the overhead water sample.

In the illustrated embodiment, the membrane 44 surrounds the chloride specific electrode 32. Any ion selective electrode can be used. Preferably, a silver silver chloride electrode is used. Such an electrode is available from Omega of Stanford, Conn. under the designation ISE 8760. In the preferred embodiment illustrated, the measurement cell 30 includes a reference electrode 34. Such a reference electrode is available from Omega under the designation PHE 3211. However, a single electrode, having a reference incorporated therein, can be used, if desired.

Due to the process and structure of the present invention, the chloride specific electrode can accurately monitor the chloride in the fluid stream. No sulfides will contact the chloride selective electrode to adversely effect the accuracy of this monitoring process.

Pursuant to the present invention, the process can be utilized to neutralize chloride in the fluid stream. To this end, the chloride specific electrode can be utilized to automatically, on-line monitor the chloride in the fluid stream. Heretofore, such measurements were made 3 to 5 times a week. To allow the system to control the neutralizer addition, the measurement cell 30 is connected to a CPU 46. The CPU 46 can be used to generate a signal to the neutralizing agent dispenser 9.

The neutralizing agent is introduced into the system, whether injected into the crude oil charge, an upper segment of the distillation column, or the overhead vapor line, by a neutralizer dispenser 9. The neutralizer dispenser may be any system known in the art suitable for the controlled introduction of neutralizing agent into the distillation system. A suitable neutralizing dispenser can be selected from any of several commercially available positive displacement pumps. Examples of some suitable pumps in current use include Williams Air Pumps, Milton Roy Positive Displacement Pumps, Crane Positive Displacement Pumps, and Stanmar Positive Displacement Pumps.

In contrast to some typical systems, that only allow the neutralizer feed pump to be adjusted approximately once a day, the present system will allow continuous monitoring and adjustment of neutralizer feed pump. This will prevent the pulsing of acid concentrations that may not otherwise be neutralized.

The neutralizing agents may be any conventional chemical base typically used in the neutralization of acids. The preferred neutralizing agents are anhydrous ammonia, ammonium hydroxide, phosphates, and organic amines including, but not limited to, methylpropylamine, dimethylamine, morpholine, isopropylamine and monoethanolamine. Hydroxide and carbonate salts may also serve as neutralizing agents. The selection of an appropriate neutralizing agent, and of an appropriate concentration of such agent, are within the ordinary skill in the art.

The system 7 can be utilized with a strong acid analyzer such as that disclosed in U.S. patent application Ser. No. 07/867,890. Both systems can be used to generate signals to the neutralizer pump or two separate pumps can be used.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method for measuring on-line the chloride content of a fluid in a refinery process stream that may contain sulfides comprising the steps of:
   collecting a sample of fluid from a process stream to form a sample stream;
   adding a sulfide scavenger obtained by reacting morpholine with formaldehyde to the sample stream;
   passing the sample stream through a membrane that prevents a reaction product of the sulfide scavenger and sulfide from flowing therethrough; and
   allowing the sample stream that flows through the membrane to contact a chloride specific electrode of a measurement cell to measure chloride content 2. The method of claim 1 wherein the sulfide scavenger reacts with the sulfide by way of nucleophilic substitution.

3. The method of claim 1 wherein the sulfide scavenger has a molecular weight of greater than 500.

4. The method of claim 1 wherein the sulfide scavenger is added in an amount at least twice the expected content of sulfide in the fluid.

5. The method of claim 1 wherein the sulfide scavenger is bis(morpholinyl)methane.

6. The method of claim 1 wherein the membrane is a dialysis membrane.

7. A method for neutralizing hydrochloric acid resulting from chloride in a fluid stream comprising the steps of:
   collecting a sample of fluid;
   adding a sulfide scavenger obtained by reacting morpholine with formaldehyde to the fluid;
   passing the fluid through a membrane that prevents a reaction product of the sulfide scavenger and sulfide to flow therethrough;
   allowing the fluid that flows through the membrane to contact a chloride specific electrode of a measurement cell to measure chloride content;
   generating a signal responsive to the chloride content measured by the measurement cell; and
   dispensing a neutralizer to the fluid stream in response to the signal.

8. The method of claim 7 wherein the sulfide scavenger reacts with the sulfide by way of nucleophilic substitution.

9. The method of claim 7 wherein the sulfide scavenger is bis(morpholinyl)methane.

10. The method of claim 7 wherein the sulfide scavenger has a molecular weight of greater than 500.

11. The method of claim 7 wherein the membrane is a dialysis membrane having a molecular weight cut-off of 100 or greater.

12. The method of claim 7 wherein the neutralizer is chosen from the group consisting of: a hydroxide salt; a carbonate salt, anhydrous ammonia; aqueous ammonia; phosphates; and organic amines.

13. The method of claim 12 wherein the sulfide scavenger has a molecular weight of greater than 500.

14. A method for automatically, on-line monitoring chloride levels in overhead water in an oil refinery comprising the steps of:
collecting a sample of overhead water to form a sample stream;
adding to the sample stream a sulfide scavenger obtained by reacting morpholine with formaldehyde that reacts with sulfide by way of nucleophilic substitution to create a reaction product having a molecular weight of greater than approximately 100;
passing a resultant fluid stream through a dialysis membrane that prevents the reaction product from passing therethrough; and
causing the fluid stream that passes through the membrane to contact a chloride specific electrode of a measurement cell to measure chloride content.

15. A method for measuring the chloride content of a fluid that may contain sulfides comprising the steps of:
collecting a sample of fluid;
adding a first reaction product obtained by reacting morphine with formaldehyde to the fluid;
passing the fluid through a membrane that prevents a second reaction product of the first reaction product and sulfide from flowing therethrough; and
allowing the fluid that flows through the membrane to contact a chloride specific electrode of a measurement cell to measure chloride content.

16. A method for measuring the chloride content of a fluid that may contain sulfides comprising the steps of:
collecting a sample of fluid;
adding bis(morpholinyl)methane to the fluid;
passing the fluid through a membrane that prevents a reaction product of the bis(morpholinyl)methane and sulfide from flowing therethrough; and
allowing the fluid that flows through the membrane to contact a chloride specific electrode of a measurement cell to measure chloride content.

17. A method for neutralizing chloride in a fluid stream comprising the steps of:
collecting a sample of overhead water;
adding a first reaction product obtained by reacting morpholine with formaldehyde to the fluid;
passing the fluid through a membrane that prevents a second reaction product of the first reaction product and sulfide to flow therethrough;
allowing the fluid that flows through the membrane to contact a chloride specific electrode of a measurement cell to measure chloride contents;
generating a signal responsive to the chloride content measured by the measurement cell; and
dispensing a neutralizer to the fluid stream in response to the signal.

* * * * *